United States Patent

Stevens et al.

[11] Patent Number: 5,516,758
[45] Date of Patent: May 14, 1996

[54] POLYAMIDES BEARING FUNCTIONALIZED SIDE CHAINS USEFUL AS WATER SOLUBLE HYPOLIPIDEMIC AGENTS

[75] Inventors: Kent R. Stevens, Chatam; William V. Taggart, Quakertown, both of N.J.

[73] Assignee: Berlex Laboratories, Inc., Wayne, N.J.

[21] Appl. No.: 172,310

[22] Filed: Dec. 23, 1993

Related U.S. Application Data

[63] Continuation-in-part of Ser. No. 716,883, Jun. 18, 1991, abandoned, which is a continuation-in-part of Ser. No. 543,916, Jun. 26, 1990, abandoned, which is a continuation-in-part of Ser. No. 328,014, Mar. 23, 1989, abandoned.

[30] Foreign Application Priority Data

Mar. 21, 1990 [EP] European Pat. Off. ............. 90250078
Dec. 6, 1991 [EP] European Pat. Off. ............. 91120988

[51] Int. Cl.$^6$ ............... A61K 31/785; C07D 213/20
[52] U.S. Cl. ............... 514/12; 514/357; 514/399; 514/634; 514/642
[58] Field of Search ............... 514/12, 642, 357, 514/399, 634; 525/435, 436; 528/322; 530/324; 546/336; 548/338.1

[56] References Cited

U.S. PATENT DOCUMENTS 4,314,808  2/1982  Jacquet et al. .............. 8/405

FOREIGN PATENT DOCUMENTS 7727769  4/1979  France ................. 8/405

Primary Examiner—C. Warren Ivy
Assistant Examiner—Zinna N. Davis
Attorney, Agent, or Firm—Elizabeth A. Bellamy; Diana Hamlet-King; Anthony J. Zelano

[57] ABSTRACT

This invention relates to derivatives of polyanhydroaspartic acid which are non-systemic water soluble polymers and which are intended to be lipid lowering agents. The pharmaceutical compositions/formulations incorporating these compounds are also discussed.

14 Claims, No Drawings

POLYAMIDES BEARING FUNCTIONALIZED SIDE CHAINS USEFUL AS WATER SOLUBLE HYPOLIPIDEMIC AGENTS

CROSS-REFERENCE TO RELATED APPLICATIONS

This Application is a continuation-in-part of U.S. Ser. No. 07/716,883, filed Jun. 18, 1991 now abandoned, which is a continuation-in-part of U.S. Ser. No. 07/543,916, filed Jun. 26, 1990 now abandoned, which is a continuation-in-part of U.S. Ser. No. 7/328,014, filed Mar. 23, 1989, now abandoned, all of which are entirely incorporated by reference herein.

FIELD OF INVENTION

Known non-systemic plasma cholesterol lowering agents such as cholestyramine and colestipol are administered as sequestering agents to bind bile acids in the intestinal tract. These form complexes which are excreted in the feces whereby the bile acids which would otherwise be reabsorbed and returned to the liver are removed from the body. As a result, the enterohepatic cycle is interrupted which leads to an increased metabolism of cholesterol to bile acids with a resultant decrease in plasma cholesterol levels. Both cholestyramine and colestipol are water-insoluble resins which in order to be efficacious must be taken in large bulk. Due to this dosing regimen and certain untoward side effects, patient compliance is a problem.

It is the object of this invention to provide certain polyamides which are non-systemic, water soluble polymers which are hypolipidemic agents, that is they are useful in treating hyperlipidemia wherein plasma cholesterol and/or triglyceride levels are excessive. In view of their nature, it is expected these compounds will increase patient compliance for the treatment of hyperlipidemia.

This invention relates to these water soluble polymers which are derivatives of polyanhydroaspartic acid, to their pharmaceutically acceptable salts and their pharmaceutically acceptable formulations.

GENERAL DESCRIPTION OF THE INVENTION COMPOSITION-OF-MATTER ASPECT

This invention relates to novel and known polyamides bearing functionalized side chains which are useful as non-systemic water soluble hypolipidemic agents.

The water soluble hypolipidemic compounds of this invention are of the following Formula II:

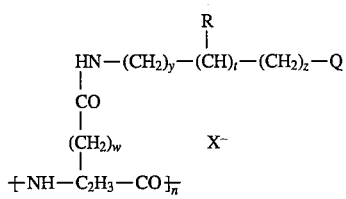

wherein
w is the integer 0 or 1;
y is the integer 1–6;
z is the integer 0–3;
t is the integer 0 or 1;

Q is 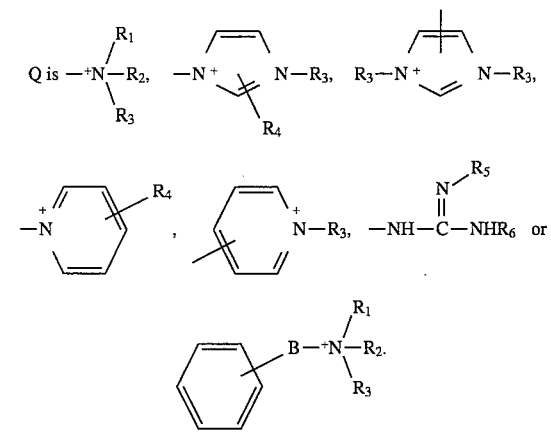

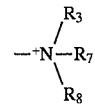

group, or when taken together form a saturated heterocyclic ring of from 5 to 6 members which may contain a

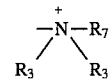

or —O— linkage;

R is hydrogen, lower alkyl, phenyl or when taken together with $R_1$ forms a saturated monoheterocyclic ring of from 5 to 6 members;

$R_1$, $R_2$ are the same or independently $C_1$–$C_{10}$ straight or branched chain alkyl which may be substituted by up to 3 substituents selected from 1 to 2 hydroxyl groups and one $R_3$ is methyl, ethyl, benzyl which may be substituted by up to 3 substituents selected from hydroxyl, halogen, methoxy and $C_1$–$C_6$ straight or branched chain alkyl, 1-naphthyl or 2-naphthyl;

$R_4$ is a $C_1$–$C_6$ straight or branched chain alkyl which may be substituted by one hydroxyl group;

$R_5$, $R_6$ are the same or independently hydrogen, $C_1$–$C_4$ straight or branched chain alkyl or when taken together form a diheterocyclic ring of from 5 to 6 members;

$R_7$, $R_8$ are the same or independently $C_1$–$C_6$ straight or branched chain alkyl which may be substituted by one hydroxyl group or when taken together with an —O— linkage form a morpholine moiety;

B is a direct link or a $C_1$–$C_4$ straight or branched chain alkyl;

n is an integer in the range from about 5 to 500; and $X^-$ is an anion forming a pharmaceutically acceptable salt.

Preferred compounds of the foregoing are those wherein w is the integer 0.

More preferred compounds are those wherein w is the integer 0 and n is in the range of 15 to 500.

Most preferred compounds are those wherein
a) w is the integer 0,
b) n is in the range of 20 to 200,
c) R is H, y is the integer 1, t is the integer 1 and z is 0 or 1.

Particularly preferred compounds are those wherein
a) w is the integer 0, b) n is in the range of 50 to 200, c) R is H, y is the integer 1, t is the integer 1 and z is 0 or 1, and d) $R_3$ is methyl or benzyl.

The foregoing compounds of Formula II which compounds are useful as hypolipidemic agents are inclusive of novel and known compounds. Said novel compounds of the invention are those defined by the following Formula I:

$$\begin{array}{c} R \\ | \\ HN-(CH_2)_y-(CH)_t-(CH_2)_z-Q \\ | \\ CO \\ | \\ (CH_2)_w \quad\quad X^- \\ | \\ \bracket{NH-C_2H_3-CO}_n \end{array} \quad\quad I$$

wherein w is the integer 0 or 1;

y is the integer 1–6;

z is the integer 0–3;

t is the integer 0 or 1;

Q is 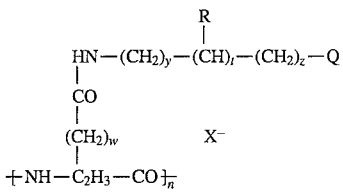

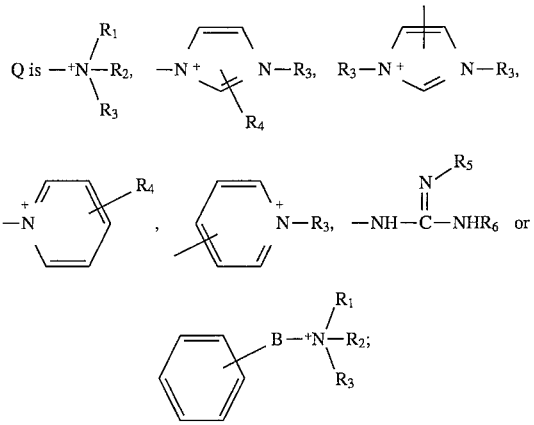

R is hydrogen, lower alkyl, phenyl or when taken together with $R_1$ forms a saturated monoheterocyclic ring of from 5 to 6 members;

$R_1$, $R_2$ are the same or independently $C_1$–$C_{10}$ straight or branched chain alkyl which may be substituted by up to 3 substituents selected from 1 to 2 hydroxyl groups and one

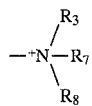

group, or when taken together form a saturated heterocyclic ring of from 5 to 6 members which may contain a

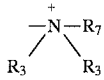

or —O— linkage;

$R_3$ is methyl, ethyl, benzyl which may be substituted by up to 3 substituents selected from hydroxyl, methoxy, halogen and $C_1$–$C_6$ straight or branched chain alkyl, 1-naphthyl or 2-naphthyl;

$R_4$ is $C_1$–$C_6$ straight or branched chain alkyl which may be substituted by one hydroxyl group;

$R_5$, $R_6$ are the same or independently hydrogen, $C_1$–$C_4$ straight or branched chain alkyl or when taken together form a diheterocyclic ring of from 5 to 6 members;

$R_7$, $R_8$ are the same or independently $C_1$–$C_6$ straight or branched chain alkyl which may be substituted by one hydroxyl group or when taken together with an —O— linkage form a morpholine moiety;

B is a direct link or a $C_1$–$C_4$ straight or branched chain alkyl;

n is the integer in the range from about 5 to 500; and $X^-$ is an anion forming a pharmaceutically acceptable salt.

The foregoing novel compounds of Formula I are inclusive of the provisos that when R is hydrogen and Q is

then $R_3$ cannot be methyl or ethyl when a) one or both of $R_1$ and $R_2$ is a $C_1$–$C_{10}$ straight or branched chain unsubstituted alkyl, b) $R_1$ and $R_2$ together form a 6 membered monoheterocyclic or diheterocyclic oxygen containing ring.

It is to be understood that the definition of the compounds of Formulae I and II encompass all possible stereoisomers and mixtures thereof which possess the activity discussed below. In particular, it encompasses racemic modifications and any optical isomers which possess the individual activity.

It is also understood that the definition of the compounds of Formula I and II encompasses all possible polymorphic modifications and other solid state modifications which possess the stated activity.

As contemplated herein, the pharmaceutically acceptable anion $X^-$ is inclusive of, for instance, halide (preferably chloride), acetate, citrate, propionate, phosphate, sulfate and mono methyl sulfate.

In the foregoing Formulae I & II, the term lower alkyl shall refer to a $C_1$–$C_4$ straight or branched carbon chain as for instance methyl, ethyl, propyl, isopropyl, butyl, sec-butyl, and tertiary butyl.

As depicted in the following Schemes and in the Process Aspect and in the Formulae I and II, the —$C_2H_3$— group can represent either the —CH—$CH_2$— group or the

group. Thus in Formula II the groups can either be depicted as

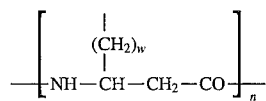

or be depicted as

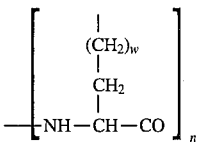

or even mixtures thereof.

The compounds of the invention have backbones derived from polyanhydroaspartic acid or polyglutamate. Considered as equivalents to this invention are co-polymers of the type as exemplified in Formula 7. Also considered as equivalents are those potentially branched or cross-linked polymers of the type as exemplified by Examples XII, XIII, and XVIII. In general, this invention includes homo- and copolymers having monomeric units of the formula [NH—$C_2H_3A$—CO] where A is $(CH_2)_w$—CO—HN—$(CH_2)_y$—(CH)$_r$R—$(CH_2)_z$—Q, wherein the variables are as defined above, and wherein individual monomeric units may be the same or different and the overall number of monomeric units is defined above.

The compounds which follow are some of those which serve to exemplify various aspects of the invention described herein.

A. Poly[imino[1-[2-[[[5-[(3-chlorophenyl)methyl- 2-hydroxyethyl(propyl)ammonio]-3-phenylpentyl]amino] carbonyl]ethyl]-2-oxo-1,2-ethanediyl chloride]].

B. Poly[imino[1-[[[[5-[[2-[4-methylmorpholinium-4-yl]-ethyl]- 2-hydroxyethyl(methyl)ammonio]pentyl] amino]carbonyl] methyl]-2-oxo-1,2-ethanediyl dicitrate]].

C. Poly[imino[1-[[[[[1-methyl-1-naphthalenylpiperidinium- 4-yl]methyl]amino]carbonyl]methyl]-2-oxo-1,2-ethanediyl chloride]].

D. Poly[imino[1-[[[[1-(phenylmethyl)-1-[2-[4-methyl-morpholinium- 4-yl]ethyl]piperidinium-4-yl] methyl] amino]carbonyl]methyl]-2-oxo- 1,2-ethanediyl dichloride]].

E. Poly[imino[1-[[[3-[[3-[ethyl(methyl)propylammonio] propyl]- 2-(trimethylammonio)ethyl(methyl)ammonio] propyl] amino]carbonyl]methyl]-2-oxo-1,2-ethanediyl trichloride]].

F. Poly[imino[1-[2-[[[4-[1-ethyl-4,4-di(phenylmethyl)piperazinium- 1-yl]butyl]amino]carbonyl]ethyl]-2-oxo- 1,2-ethanediyl diphosphate]].

G. Poly[imino[1-[[[[3-[[[[(1-methylethylamino)1-methylethylimino] methyl]amino]methyl]pentyl]amino]carbonyl]methyl]- 2-oxo-1,2-ethanediyl]]hydrochloride.

It has now been discovered that this invention is fully applicable for values of n=5 to <50. Originally, the lower limit for n was felt to be 50. Preferred lower limits were even higher. Thus, this invention now surprisingly includes ranges such as those having as lower or upper limits values such as 49, 48, 47, 46, 45, 40, 35, 30, 25, 20, 15, 10, 5, etc. Consequently, suitable new ranges for this invention includes ranges such as 5–49, 10–49, 10–45, 20–45, 5–500, 10–500, 25–500, 50–500 etc.

PROCESS ASPECT

The compounds of this invention can be prepared, in general, by standard techniques analogous to those know in the art. The general process is characterized in that polyanhydroaspartic acid of the Formula 1, in which n is an integer from 5 to 500, is reacted with at least one amine of the Formula 2 where A is a non-quaternized Q lacking $R_3$.

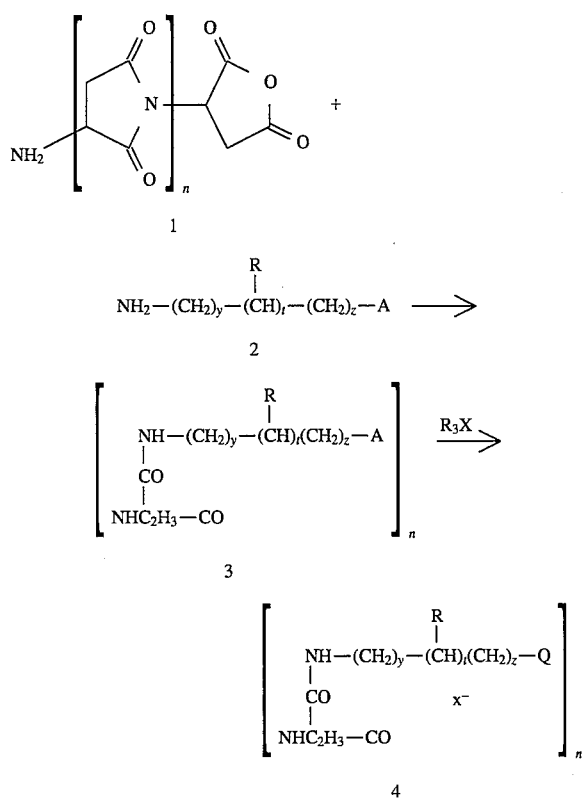

SCHEME I

The amidation reaction can bring an amine onto all the reactive imide sites of the polyanhydroaspartic acid, or onto a fraction of said reactive sites, in which case the reaction can be followed by an amidation reaction with one or several other amines having the Formula 2. For complete amidation reaction, $m_1$ moles of amine are being reacted per mole (monomer basis) of polyanhydroaspartic acid, $m_1$ being an integral or non-integral number between 1 and 15. In the case where more than one amine is reacted with polyanhydroaspartic acid, the amines can be added sequentially at a quantity of $m_1$ being a fraction between 0 and 1 for the first amine, and $m_2$ being equal to or greater than $1-m_1$ for the second amine.

The amidation reactions are generally carried out in a solvent such as dimethylformamide (DMF), although dimethylsulfoxide (DMSO) can also be used. Reactions may be run at room temperature to about 75° C. Reaction times are generally in the range of 2–72 hours depending on the reaction temperature and the amine. The products of the amidation reaction may be isolated by, for example, precipitation from the reaction mixture with a non-solvent or by dilution with an aqueous acid, dialysis to remove low molecular weight products, and lyophilization. The second procedure provides salts of the intermediate polymeric amines. Alternatively, the reaction mixture can be used directly in the subsequent quaternization [or guanidine formation] reaction.

The polyanhydroaspartic acid can be obtained in accordance with the methods described in the literature. As for instance, French Patent 70.24831, the polyanhydroaspartic acid is prepared by heating aspartic acid in the presence of phosphoric acid under vacuum at 170°–200° C. assuring a constant renewal of the reaction mass surface. This preparation can be carded out using a rotary evaporator to renew the surface.

The products from Scheme I of Formula 3 can be convened to the quaternary ammonium derivatives 4 by reaction with a suitable alkylating agent. The products of Formula 4 are most commonly obtained by quaternization of 3 with an excess of dimethyl sulfate, methyl chloride, methyl iodide or other alkylating agent (e.g. benzyl bromide) in, for example, DMF or methanol. In some cases it may be appropriate to add a cosolvent such as water to prevent the precipitation of partially quaternized species. The quaternization of 3 to give 4 may be conducted at temperatures ranging from about room temperature to about 100° C. depending on the reactivities of 3 and the alkylating agent. When gaseous or low boiling alkylating agents are employed, it may be necessary to conduct the quaternization under pressure. Depending on the reactivities, reaction times for the quaternization step are generally in the range of 2–48 hours. An insoluble base such as potassium or calcium carbonate may be added as a proton scavenger. This is necessary if the group A is —$NH_2$ or NHR, and also if a salt form of Formula 3 (such as hydrochloride) is used in the reaction. Such bases may be used in excess, from 1 to 5 equivalents. In the cases where the quaternization is difficult, heating the reaction mixture for longer times, or using a more reactive alkylating agent such as methyl trifluoromethanesulfonate may be appropriate.

Insofar as the anion $X^-$ is concerned in the foregoing scheme, used in conjunction with describing the polymer 4, a wide variety of anions are useful herein, a criterion being the pharmaceutically acceptable nature of such. Suitable anions include, for example, halides, acetate, citrate, propionate, mono methyl sulfate, sulfate and phosphate, chloride being preferred.

Replacement of the counter anion $X^-$ in these polymers with other pharmaceutically acceptable anions may be accomplished by methods well known to the art. For example, diluted polymer solutions can be treated with insoluble anion exchange resins in the hydroxide form. The hydroxide salt of the polymer can then be neutralized with the appropriate acid. Preferably, diluted polymer solutions can be directly converted to the chloride anion form by treating two or more times with an excess of aqueous hydrochloric acid followed by dialysis.

Determination of the molecular weight range of the product can be carried out using standard methods known in the art. For example, average molecular weights can be determined by, for example, osmometry and light scattering, giving the number and weight average molecular weights, respectively. Relative molecular weights can be determined by gel permeation chromatography using appropriate calibration standards. Viscosity measurements on dilute solutions may also be used to give a measure of the average molecular weight.

SCHEME II

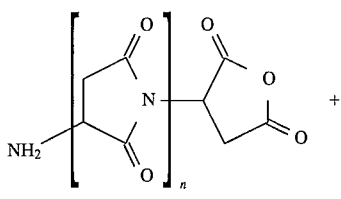

1

SCHEME II (continued)

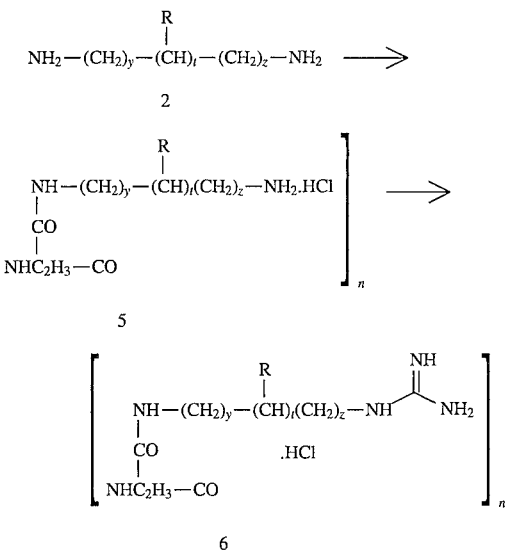

In the foregoing Scheme II where Q is a guanidinium functionality (Formula 6), the compounds of this type may be prepared by reaction of an excess of a primary diamine with polyanhydroaspartic acid. The intermediate of Formula 5 may be isolated as the hydrochloride salt and converted to the corresponding guanidinium derivative by reaction with a guanidinating agent known to the art, such as S-methylisothiouronium iodide in the presence of base.

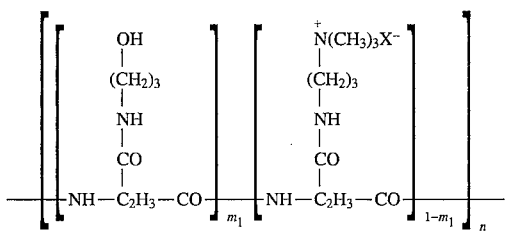

Copolymers can be developed when polyanhydroaspartic acid is reacted with two or more different amines of the Formula 2. Copolymers of the foregoing Formula 7 may also be similarly developed by first reacting with a quantity $m_1$ of 3-aminopropanol, $m_1$ being a fraction between 0 and 1. The intermediate may then be reacted with a quantity $m_2$ of 3-dimethylaminopropylamine, $m_2$ being equal to or greater than $1-m_1$. The copolymer can then be quaternized by the previously described method.

Copolymers that are potentially branched or cross-linked may be prepared by first a reaction of polyanhydroaspartic acid with a quantity $m_1$ of a primary diamine, $m_1$ being a fraction between 0 and 1 equivalents. The intermediate can then be reacted with a quantity $m_2$ of a second amine of Formula 2, $m_2$ being equal to or greater than $1-m_1$ equivalents for the second amine. These potentially branched or cross-linked copolymers can then be quaternized by the previously described method. Alternatively, polymers of Formula 3 can be reacted with various amounts of cross-linking reagents, for example, 1,4-dichloro-2-butene, and a quaternizing agent, to afford copolymers that are potentially branched or cross-linked.

SCHEME III

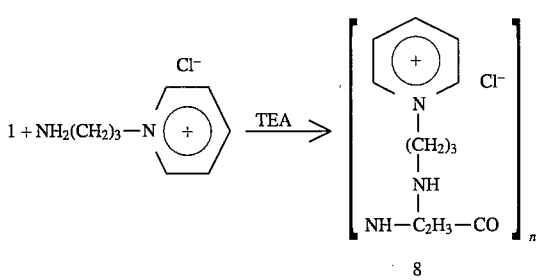

In such instances where Q is an N-substituted pyridinium derivative (Formula 8), the polymeric quaternized pyridinium derivative may be prepared in one step as in the foregoing Scheme III, by reaction of 3-aminopropylpyridinium chloride hydrochloride and triethylamine with polyanhydroaspartic acid.

In such instances where Q is a diquaternary derivative (Formula 9), the polymeric diquaternized derivatives may be prepared by the generalized process of amidation with excess amine (triamine) followed by quaternization with excess alkylating agent as exemplified in the following Scheme IV.

SCHEME IV

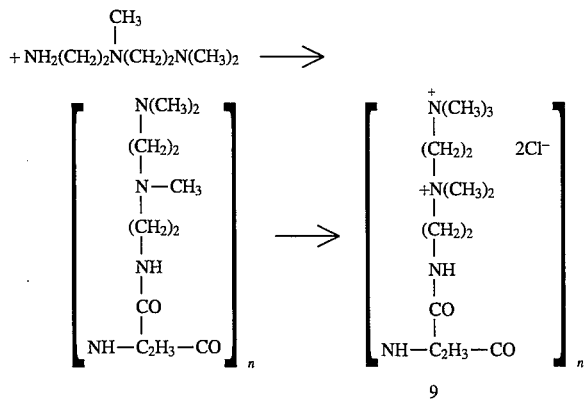

SCHEME V

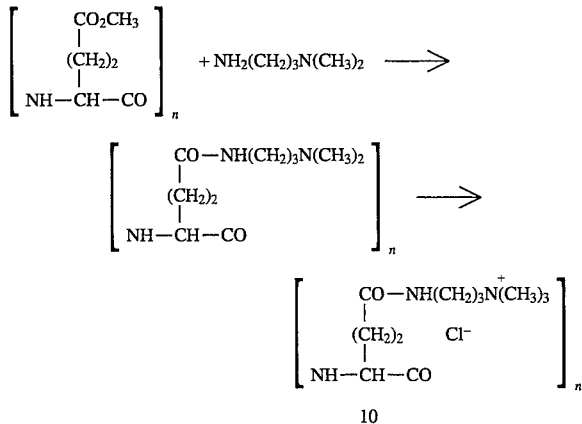

In the above Scheme V, polyglutamide derivatives (Formula 10) may be prepared by standard techniques analogous to those known in the art. Poly(γ-methyl L-glutamate) can be reacted with N,N-dimethyl-1,3-propanediamine, quaternized with dimethyl sulfate, and ion exchanged with hydrochloric acid to afford a polymer of Formula 10.

In the overall process, as exemplified in the Schemes above, the degree of polymerization (that is, the number of repeating monomer units in the polymer, which determines the molecular weight) can be influenced by various factors. These are discussed separately below; it is to be understood that any or all of these factors may be adjusted so as to give a final product with a desired degree of polymerization.

The degree of polymerization of the starting polyanhydroaspartic acid determines the upper limit on the degree of polymerization of the final product. Thus, higher molecular weight polyanhydroaspartic acid will lead to higher molecular weight final product, all other process parameters being kept the same. The degree of polymerization of the polyanhydroaspartic acid can be adjusted by the conditions used in its formation, as would be predicted by one skilled in the art. Thus, if the polyanhydroaspartic acid is prepared as in French patent 70.24831 as described above, higher reaction temperatures, longer reaction times, and greater relative quantities of polyphosphoric acid tend to give polyanhydroaspartic acid with a higher degree of polymerization, that is, with a higher molecular weight. Lower temperatures, shorter reaction times, and smaller proportions of polyphosphoric acid tend to give polyanhydroaspartic acid with a lower degree of polymerization.

The conditions in the amidation reaction influence the degree of polymerization of the final product, owing to the possibility of cleavage of the polymeric backbone by the amine reagent. The dependence of this cleavage on reaction conditions is apparent to one skilled in the art. Thus, in this reaction if, the first step in Scheme I, is conducted at higher temperatures, for longer times, or with greater quantities of amine reagent 2, the degree of polymerization of the resulting intermediate 3 tends to be lower than if lower temperatures, shorter reaction times, or smaller excesses of amine reagent are used. When the mildest conditions and the smallest practical excess of amine are used, the degree of polymerization of the intermediate tends to more nearly equal the degree of polymerization of the starting polyanhydroaspartic acid.

By exposing either the intermediate 3 in Scheme I, or the final product in any of the Schemes, to conditions of aqueous acid, the degree of polymerization may be lowered owing to hydrolysis of the amide linkages in the polymer backbone. The trends are as predicted by one skilled in the art. For example, exposing the intermediate 3 or the final product to more concentrated acid, or conducting said exposure for longer times or at higher temperatures, will tend to give a lower degree of polymerization than would result from using more dilute acid, shorter exposure times, or lower temperature. When conversion of the product into the chloride anion form is conducted as described above, by treating the polymer solution with aqueous hydrochloric acid followed by dialysis, the degree of polymerization simultaneously can be lowered to any desired degree by appropriate selection of the conditions for the hydrochloric acid treatment.

The degree of polymerization of the product can be influenced by the means by which the product is isolated. Most methods for isolation of water soluble polymers may be used, and the selection of the appropriate conditions would be apparent to one skilled in the art. For example, when dialysis is employed as part of the isolation procedure, the nominal molecular weight cutoff of the dialysis membranes can be chosen so as to retain the fraction of the polymer with a molecular weight above a chosen approximate value, with material of lower molecular weight passing through the membrane. Alternately, fractionation can be achieved by partially precipitating the product from aqueous solution by the addition of appropriately chosen volumes of a water miscible non-solvent such as acetone or 2-propanol; the precipitated fraction is relatively enriched in the higher molecular weight molecules while the supernatant solution is enriched in lower molecular weight molecules. Fractionation can also be achieved by preparative gel permeation chromatography, and by other means known in the art.

METHOD OF USE AND PHARMACEUTICAL COMPOSITION ASPECT

Clinical results demonstrating that in man a 1% reduction in serum cholesterol level results in a 2% reduction in coronary heart disease incidence have led the National Cholesterol Education Program Expert Panel to designate bile acid sequestrants as preferred first line therapy in familial hyperlipidemia patients who are at high risk of coronary heart disease, even ahead of systemic lipid lowering drugs such as HMG-CoA-reductase inhibitors (lovastatin). However, the observed clinical synergy between bile acid sequestrants and HMG-CoA-reductase inhibitors in the reduction of serum cholesterol suggests a further importance for the future of bile acid sequestrant therapy.

The liver is the primary source of the plasma cholesterol produced in humans. Bile acids are major end products of cholesterol catabolism which aid in fat digestion. A bile acid pool a portion of which is normally excreted via the feces daily is maintained in the body by enterohepatic cycling. Bile acid sequestrants act by-definition to facilitate the removal of bile acids from their normal enterohepatic cycle in the G.I. tract. This modification of bile acid excretion has the effect in certain mammals including man of enhancing the conversion of cholesterol to bile acids. This leads to an increase in liver β-lipoprotein receptors as well as a compensatory increase in the rate of hepatic biosynthesis of cholesterol both of which serve to maintain hepatic cholesterol balance. More importantly a resultant lowering of serum low density lipoproteins and cholesterol is observed. In other words, the lower level of available bile acids (from sequestration)in turn, requires the biosynthesis of replacement bile acids from cholesterol. It is estimated that about one third of cholesterol turnover in the body is attributable to bile acid synthesis. Forcing the body to make more bile acids is therefore a means of reducing plasma and tissue stores of cholesterol.

An object of the compounds of this invention is to provide hypolipidemic agents which will be easy to administer thereby allowing for greater patient compliance to achieve the full efficacy potential of these agents. As hypolipidemic agents they will reduce the lipids in a hyperlipidemic mammal especially humans in need of such lipid lowering. These compounds are non-systemic, water soluble polymers which act as lipid lowering agents by not only acting as bile acid sequestrants thereby lowering serum cholesterol, but they have also been found to lower triglycerides.

The compounds of the present invention have been found to be more effective than cholestyramine in depleting bile deoxycholate and thus they reduce the lithogenicity of bile. The polyanhydroaspartate derived polymers are thus potentially useful in dissolving, delaying progression and/or blocking formation of gallstones in humans. The mechanism of depletion of deoxycholate may be related to the ability of these compounds to inhibit the growth of gram positive bacteria which are known to have the capability to reduce cholic acid to deoxycholic acid and chenodeoxycholic acid to lithocholic acid. Thus, if the primary bile acids, cholic acid and chenodeoxycholic acid are prevented from conversion to the secondary bile acids, deoxycholic acid and lithocholic acid respectively—deoxycholate is reduced.

Deoxycholic acid brings in more than its proportionate share of cholesterols to bile, therefore if deoxycholic acid is reduced the quantity of cholesterol in bile is reduced. Further, from those observations the lithogenicity (stone-forming) properties of the bile is reduced. Still further, chenodeoxycholic acid is a known gall-stone dissolving agent therefore it's non-degration should also aid the reduction of lithogenicity.

As stated above the compounds of the present invention have been found to have gram positive bacterial inhibitory effects.

The following Table VI identifies the types of gram positive and certain gram negative bacteria against which the compounds were tested. Some of these bacteria are found in the intestinal tract of animals and man, other bacteria are associated with man as direct pathogens, food borne pathogens or environmental cohabitants.

TABLE VI

| GRAM POSITIVE BACTERIA | GRAM NEGATIVE BACTERIA |
|---|---|
| Eubacterium sp. 12708* | Escherichia coli Hb101 |
| Clostridium scindens* | Bacteroides fragilis# |
| Clostridium difficile | Bacteroides vulgatus |
| Clostridium perfringens**# | Pseudomonas aeruginosa |
| Listeria monocytogenes** | Helicobacter pylori |
| Bacillus cerus | |
| Staphylococcus auereus** | |
| Propionibacterium acnes | |
| Streptococcus mutans | |

*Bacteria which are known to metabolize bile acids
Bacteria which are known to deconjugate bile salts
**Potential food pathogens The bacteria to be tested were grown overnight in the appropriate medium which medium would be obvious to those skilled in the art. Approximately 0.5 mL of the overnight culture was used to inoculate 4.5 mL fresh sterile medium with or without water-soluble polymer. Growth was monitored by measuring the changes in turbidity versus time using a Klett-Summerson colorimeter (red filter). The calculation of the percent inhibition of growth was accomplished by subtracting the turbidity value at the end of the log phase of growth of the untreated control bacteria from the turbidity at the beginning of the growth phase. The same change in turbidity was determined for the treated bacteria. The value for the treated bacteria subtracted from the control value divided by the control value times 100 gives the percent inhibition of growth.

The compounds tested and for which results are given in the following tables are as follows:

Poly[imino[1-[[[[3-(trimethylammonio)propyl]amino] carbonyl]methyl]-2- oxo- 1,2-ethanediyl chloride]] (Compound A);

Poly[imino[1-[[[[2-[[2-(trimethylammonio)ethyl]dimethylammonio]ethyl]amino] carbonyl]methyl]-2-oxo-1,2-ethanediyl chloride]] (Compound B);

Poly[imino[1-[[[[3-[dimethyl(phenylmethyl)ammonio] propyl]aminocarbonyl] methyl]-2-oxo-1,2-ethanediyl chloride]] (Compound E);

Poly[imino[1-[[[[3-[(aminoiminomethyl)amino]propyl]amino]carbonyl] methyl]-2-oxo-1,2-ethanediyl hydrochloride]] (Compound F);

[S]-poly[imino[1-[[[[3-(trimethylammonio )propyl]amino]carbonyl] methyl]-2-oxo-1,2-ethanediyl chloride]] (Compound G).

Compound B was tested as both a low molecular weight (LMW) and high molecular weight (HMW) molecule.

The following Tables VII–XI are illustrative of the dose responses for the various compounds of the invention against various bacteria.

TABLE VII

INHIBITION OF BACTERIAL GROWTH: DOSE REPONSE (% Inhibition)

| BAC- | Eubacterium sp. 12708 | | Cl. difficle |
|---|---|---|---|
| TERIA Conc.* | Compound B LMW | Compound A | Compound B LMW |
| 0.01 | 91.7 | 77.0 | 96.2 |
| 0.025 | 94.4 | ND | 96.2 |
| 0.05 | 93.1 | 87.1 | 98.7 |
| 0.1 | 97.2 | 81.5 | 95.6 |

*The concentration of drug in the broth as percent [(WN)/V]
ND not studied

TABLE VIII

| Percent Inhibition of Growth of Eubacterium sp. 12708 | | | | | | |
|---|---|---|---|---|---|---|
| Compound | B(LMW) | B(HMW) | A | F | E | G |
| conc. 0.5% | 106 | 91 | 94 | 98 | 104 | 93 |
| conc. 1.0% | 110 | 96 | 98 | 96 | 100 | 94 |

TABLE IX

| Percent Inhibition of Growth of Escherichia coli Hb101 | | |
|---|---|---|
| Compound | F | E |
| conc. 0.5% | 98 | 104 |
| conc. 1.0% | 96 | 100 |

TABLE X

INHIBITION OF THE GROWTH OF BACTERIA BY COMPOUND A
Gram positive bacteria

| Dose Bacteria | conc. 0.025% | conc. 0.1% | conc. 0.5% |
|---|---|---|---|
| Eubacterium sp. 12708 | N/D | 81.5 | 84.3 |
| Listeria monocytogenes | 23.4 | 68.8 | 79.2 |
| Propionibacterium Acnes | 65.2 | 62.3 | 63.8 |
| Streptococcus mutans | 15.3 | 63.1 | 67.0 |

*The concentration of drug in the broth as percent [(WN)/V]

TABLE XI

INHIBITION OF THE GROWTH OF BACTERIA BY COMPOUND B
Gram positive bacteria

| Dose | conc. 0.025% | conc. 0.1% | conc. 0.5% |
|---|---|---|---|
| Eubacterium sp. 12708 | 94.4 | 97.2 | 106 |

TABLE XI-continued

INHIBITION OF THE GROWTH OF BACTERIA BY COMPOUND B
Gram positive bacteria

| Dose | conc. 0.025% | conc. 0.1% | conc. 0.5% |
|---|---|---|---|
| Clostridium scindens | N/D | N/D | 81.1 |
| Clostridium difficle | 96.2 | 95.5 | N/D |
| Listeria monocytogenes | 82.5 | 96.6 | 102 |
| Bacillus cerus | 5.2 | 76.7 | 91.1 |
| Propionibacterium Acnes | 61.5 | 61.5 | 65.2 |
| Streptococcus mutans | 67.1 | 81.4 | 89.0 |

*The concentration of drug in the broth as percent [(W/V)V]

These compounds are potent inhibitors of gram positive bacteria, and can be administered to a subject who is displaying signs of gut gram positive over-growth caused when the gut is empty and the subject has been maintained with iv feeding or when there is an overgrowth on non-susceptible bacteria caused by antibiotic therapy. For instance, the overgrowth of Cl. difficle during lincomycin therapy which causes ulcerative colitis.

Still further, since these are water soluble agents they are useful in treating food substances to inhibit the growth of gram positive bacteria that can result in food poisoning. For instance, when fresh fish are readied for market they could be sprayed with a water solution of the compound or dipped in a solution of the compound in order to reduce the possible growth of Listeria monocytogenes and other susceptible gram positive bacteria. Even further, the compounds could be added to dairy products to prevent growth of susceptible gram positive bacteria thus promoting/prolonging the products' shelf life.

The polymeric agents of this invention are highly charged and highly flexible entities. Due to these properties these agents are literally extremely sticky and are able to coat biological and non-biological surfaces. It has been found that these agents can coat the stomach lining and act as gastro-protective agents—that is the compounds of this invention are useful as gastro-protective agents in a subject in need thereof in much the same manner as the agent sucralfate.

Compound B was tested in the Sprague Dawley rat—with ethanol induced gastric lesions utilizing the following protocol.

In a rat model of acute ethanol-induced gastric injury, the oral pretreatment with 1875 mg Compound B/kg one hour prior to the oral administration of ethanol (1 mL/rat) prevented or markedly reduced ethanol-induced gastric injury. One hour after dosing with ethanol, the cumulative length of gastric lesions in control rats (n=5) pretreated with distilled water ranged from 71 to 134 mm (mean=113 mm) and the length of lesions in rats (n=5) pretreated with Compound B ranged from 0 to 5 mm (mean=2.5 mm). Twenty four hours after ethanol administration, a similar reduction of the cumulative length of gastric lesions was observed in 4 of 5 Compound B pretreated rats (range, 0 to 4 mm) as compared to 5 distilled water pretreated rats (21 to 106 mm). Cholestyramine (1875 mg/kg) (n=2) administered orally 1 hours prior to ethanol did not appear to protect the gastric mucosa (cumulative length of gastric lesions 24 to 83 mm).

The control rats developed multifocal mild to moderate mucosal necrosis/erosions which were generalized throughout the gastric mucosa. The mucosal lesions were generally accompanied by mucosal hemorrhage and submucosal edema and persisted up to 24 hours. Compound B pretreated rats developed markedly less severe lesions, generally characterized as minimal or mild focal lesions with only minimal submucosal edema, or were totally lesion-free.

The following Table XII illustrates the foregoing.

TABLE XII

| | Cumulative Length of Gross Gastric Lesions (mm) | | |
|---|---|---|---|
| NECROPSY INTERVAL | CONTROL | COMPOUND B (1875 mg/kg) | CHOLES- TYRAMINE (1875 mg/kg) |
| 1 Hour | 115 | 1 | 83 |
| | 115 | 0 | 24 |
| | 91 | 0 | — |
| | 134 | 5 | — |
| | 71 | 4 | — |
| 24 Hours | 21 | 0 | — |
| | 106 | 1 | — |
| | 44 | 3 | — |
| | 39 | 21 | — |
| | 36 | 4 | — |

The compounds of the invention when administered orally for the foregoing disease states would be cojoined with pharmaceutically acceptable carriers when necessary/appropriate. It is contemplated that such carriers might for example involve flavoring agents especially if the preparation is in the form of a syrup. They might also be given as a capsule or after lyophilization compressed into tablets, or packaged as individual sachets to be admixed with some liquid (e.g. fruit juice) or packed in bulk form. Suitable doses are in the range of 3–35 gm per day.

The invention described herein above is illustrated below in the Examples, which, however are not to be construed as limiting the scope of this invention.

EXAMPLE I

Poly[imino[1-[[[[3-(trimethylammonio) propyl]amino] carbonyl]methyl]-2-oxo-1,2-ethanediyl chloride]]

3.5 g of polyanhydroaspartic acid is dissolved in 30 mL of anhydrous DMF and added dropwise to 9.2 g of N,N-dimethyl-1,3-propanediamine while keeping the temperature of the reaction mixture below 30° C. The mixture is stirred under a nitrogen atmosphere for 18 hours at room temperature, then precipitated with a mixture of ether and petroleum ether. The precipitate is dissolved in a minimum amount of methanol and reprecipitated with ether. The precipitate is dissolved in 100 mL of methanol, and to this solution is added 25.0 g of potassium carbonate and 22.7 g of dimethyl sulfate over 0.5 h. The mixture is stirred 18 h at room temperature, then filtered and precipitated with ether. The precipitate is dissolved in 500 mL $H_2O$ and acidified with 30 mL concentrated hydrochloric acid. The solution is dialyzed while maintaining the volume constant by addition of deionized water until the effluent is pH=3. An additional 30 mL of concentrated hydrochloric acid is added and the solution is redialyzed until the effluent is pH=6. The solution is concentrated by dialysis to 100 mL and lyophilized to afford the water soluble title compound.

% Cl Calc. 14.20 Found 13.19

Cl/N Calc. 0.84 Found 0.84

C/N Calc. 2.86 Found 2.89

EXAMPLE II

In a manner similar to Example I, the following compounds
a) N,N-dimethylethanediamine,
b) N,N-dimethyl-1,4-benzenedimethanamine,
c) 1-pyrrolidinethanamine,
d) 4-morpholinepropanamine,
e) 1-piperidinethanamine,
f) N,N-dibutylpropanediamine,
g) N,N-diethylpropanediamine,
h) N,N-dimethylhexanediamine,
i) N,N-dimethylbutanediamine,
j) [4-(dimethylamino)phenyl]methanamine,
k) N,N-bis(2-hydroxyethyl)ethanediamine and
l) 1-1H-imidazolepropanamine,
are reacted with polyanhydroaspartic acid to produce respectively:

m) poly[imino[1-[[[[2-(trimethylammonio)ethyl]amino] carbonyl] methyl]-2-oxo-1,2-ethanediyl chloride]], n) poly[imino[1-[[[[4-[(trimethylammonio)methyl]phenyl] methyl]amino]carbonyl]methyl]-2-oxo- 1,2-ethanediyl chloride]], o) poly[imino[1-[[[[2-[1-methylpyrrolidinium-1-yl]ethyl] amino]carbonyl]methyl]-2-oxo-1,2-ethanediyl chloride]], p) poly[imino[1-[[[[3-]4-methylmorpholinium-4-yl]propyl] amino]carbonyl]methyl]-2-oxo-1,2-ethanediyl chloride]], q) poly[imino[1-[[[[2-[1-methylpiperidinium-1-yl]ethyl] amino] carbonyl]methyl]-2-oxo-1,2-ethanediyl chloride]], r) poly[imino[1-[[[[3-[dibutyl(methyl)ammonio]propyl] amino] carbonyl]methyl]-2-oxo-1,2-ethanediyl chloride]], s) poly[imino[1-[[[[3-[diethyl(methyl)ammonio]propyl] amino]carbonyl]methyl]-2-oxo-1,2-ethanediyl chloride]], t) poly[imino[1-[[[[6-(trimethylammonio)hexyl]amino] carbonyl] methyl]-2-oxo-1,2-ethanediyl chloride]], u) poly[imino[1-[[[[4-(trimethylammonio)butyl]amino] carbonyl] methyl]-2-oxo-1,2-ethanediyl chloride]], v) poly[imino[1-[[[[4-(trimethylammonio )phenyl]methyl]amino] carbonyl]methyl]-2-oxo-1,2-ethanediyl chloride]], w) poly[imino[1-[[[[2-[bis(2-hydroxyethyl)methylammonio] ethyl]amino]carbonyl]methyl]-2-oxo-1,2-ethanediyl chloride]] and x) poly[imino[1-[[[[3-3-methylimidazolium-1-yl)propyl] amino]carbonyl]methyl]-2-oxo-1,2-ethanediyl chloride]].

EXAMPLE III

Poly[imino[1-[[[[3-[(dimethyl)(phenylmethyl) ammonio]propyl] aminocarbonyl]methyl]-2-oxo-1,2-ethanediyl chloride]]

3.5 g of polyanhydroaspartic acid is dissolved in 30 mL of anhydrous DMF and added dropwise to 9.2 g of N,N-dimethyl-1,3-propanediamine while keeping the temperature of the reaction mixture below 30° C. The mixture is stirred under a nitrogen atmosphere for 18 h at room temperature, then precipitated with a mixture of ether and petroleum ether. The precipitate is dissolved in a minimum amount of methanol and reprecipitated with ether. The precipitate is dissolved in 200 mL of methanol, and to this solution is added 25.0 g of potassium carbonate and 22.8 g of benzyl chloride. The mixture is stirred for 48 h at 50° C., then is filtered and precipitated with ether. The precipitate is dissolved in 500 mL H$_2$O and acidified with 30 mL concentrated hydrochloric acid. The solution is dialyzed while maintaining the volume constant by addition of deionized water until the effluent is pH=6. The solution is concentrated by dialysis to 100 mL and lyophilized to afford the water soluble title compound.

% Cl Calc., 10.88 Found 8.99
Cl/N Calc., 0.84 Found 0.78
C/N Calc., 4.57 Found 4.61

EXAMPLE IV

Poly[imino[1-[[[[2-[(dimethyl)(phenylmethyl) ammonio]ethyl] amino]carbonyl]methyl]-2-1,2-ethanediyl chloride]]

In a manner similar to Example III, 2-(dimethylamino-)ethylamine is reacted with polyanhydroaspartic acid and then with benzyl chloride to produce the water soluble title compound.

EXAMPLE V

Poly[imino[1-[[[2-(1-methylpyridinium-2-yl) ethyl]amino]carbonyl] methyl]-2-oxo-1,2-ethanediyl chloride]]

1.5 g of polyanhydroaspartic acid is dissolved in 25 mL of anhydrous DMF and is added to 4.7 g of 2-pyridinethanamine. The mixture is stirred under a nitrogen atmosphere at 70° C. for 18 h, then precipitated with ether. The precipitate is dissolved in a minimum amount of methanol and reprecipitated with ether. The precipitate is dissolved in 35 mL of DMF, and to this solution is added 6.0 g of methyl trifluoromethanesulfonate. The mixture is stirred 18 h at room temperature, then precipitated with ether. The precipitate is dissolved in 300 mL H$_2$O and acidified with 10 mL concentrated hydrochloric acid. The solution is dialyzed as per Ex. I until the effluent is pH=3. An additional 10 mL of concentrated hydrochloric acid is added and the solution is dialyzed until the effluent is pH=6. The solution is concentrated by dialysis to 100 mL and lyophilized to afford the water soluble title compound.

% Cl Calc., 13.14 Found 9.13
Cl/N Calc., 0.84 Found 0.60
C/N Calc., 3.43 Found 3.36

EXAMPLE VI

Poly[imino[1-[[[[3-(1,3-dimethylimidazolium-2-yl) propyl]amino] carbonyl]methyl]-2-oxo-1,2-ethanediyl chloride]

1.5 g of polyanhydroaspartic acid is dissolved in 35 mL of anhydrous DMF and added to 5.4 g of 1-methyl-2-1H-imidazolepropanamine. The mixture is stirred under a nitrogen atmosphere at 75° C. for 40 h, then precipitated with a mixture of ether and petroleum ether. The precipitate is dissolved in a minimum amount of methanol and reprecipitated with ether. The precipitate is dissolved in 200 mL of methanol, and to this solution is added 10.6 g of potassium carbonate and 9.7 g of dimethyl sulfate. The mixture is filtered and precipitated with ether. The precipitate is dissolved in 300 mL H$_2$O and acidified with 10 mL concentrated hydrochloric acid. The solution is dialyzed as per Ex. I until the pH=3. An additional 10 mL of concentrated hydrochloric acid is added and the solution is dialyzed until the effluent is pH=6. The solution is concentrated via dialysis to 100 mL and lyophilized to afford the water soluble title compound.

% Cl Calc., 12.36 Found 8.53
Cl/N Calc., 0.63 Found 0.47
C/N Calc., 2.57 Found 2.63

EXAMPLE VII

Poly[imino[1-[[[[2-(1,3-dimethylimidazolium-4-yl) ethyl]amino]carbonyl]methyl]- 2-oxo-1,2-ethanediyl chloride]]

3.1 g of polyanhydroaspartic acid is dissolved in 35 mL of anhydrous DMF and added to 8.9 g of 4-1H-imidazolethanamine. The mixture is stirred under a nitrogen atmosphere for 24 h at 75° C., cooled to room temperature, then precipitated with ether. The precipitate is dissolved in 500 mL of DMF, and to this solution is added 130 g of potassium carbonate followed by 120 g of dimethyl sulfate dropwise over 2 h. The mixture is stirred for 18 h at 75° C., then is filtered and precipitated with ether. The precipitate is dissolved in 150 mL 1N hydrochloric acid, and dialyzed as per Ex. I until the effluent is pH=3. An additional 150 mL of 1N hydrochloric acid is added and the solution is redialyzed until the effluent is pH=6. The solution is concentrated by dialysis to 100 mL and lyophilized to afford the water soluble title compound.

% Cl Calc., 13.10 Found 9.43
Cl/N Calc., 0.63 Found 0.49
C/N Calc., 2.36 Found 2.45

EXAMPLE VIII

Poly[imino[1-[[[[3-[(aminoiminomethyl)amino]propyl] amino]carbonyl] methyl]-2-oxo-1,2-ethanediyl hydrochloride 35 g of polyanhydroaspartic acid is dissolved in 300 mL of anhydrous DMF and added to a solution of 266 g 1,3-propanediamine in 500 mL of DMF. The mixture is stirred under a nitrogen atmosphere for three days at room temperature, then precipitated with ether. The precipitate is dissolved in 6 L of water, acidified with concentrated hydrochloric acid to pH=1, dialyzed until the effluent is pH=3, then lyophilized to afford 62.3 g of a water soluble solid. 98.4 g of methylisothiouronium iodide is dissolved in 480 mL of 1.0M sodium hydroxide and 750 mL of methanol. The above water soluble solid is added, and the mixture is stirred for five days under a nitrogen atmosphere at room temperature. The reaction mixture is then acidified with 625 mL of 6N hydrochloric acid, diluted to 10 L with water, and then dialyzed as per Ex. I until the effluent is pH=3. An additional 625 mL of 6N hydrochloric acid is added and the solution is redialyzed until the effluent is pH=6. The solution is concentrated by dialysis to 2 L and lyophilized to afford the water soluble title compound.

Cl Calc., 14.20 Found 11.11
Cl/N Calc., 0.51 Found 0.43
C/N Calc., 1.37 Found 1.47

EXAMPLE IX

In a manner similar to Example VIII, the following reactants:
a) 1,2-ethanediamine
b) 1,4-butanediamine are reacted with polyanhydroaspartic acid and then with methyl isothiouronium chloride (or iodide) and bases to product respectively:

c) poly[imino[1-[[[[2-[(aminoiminomethyl)amino] ethyl] amino]carbonyl]methyl]-2-oxo-1,2-ethanediyl hydrochloride]] and d) poly[imino[1-[[[[4-[(aminoiminomethyl)amino] butyl] amino]carbonyl]methyl]-2-1,2-ethanediyl hydrochloride]].

EXAMPLE X

Poly[imino[1-[[[[2-[[2-(trimethylammonio)ethyl] dimethylammonio] ethyl]amino]carbonyl]methyl]-2-oxo-1,2-ethanediyldichloride]]

4.0 g of polyanhydroaspartic acid is dissolved in 40 mL of anhydrous DMF and added dropwise to 7.2 g of N-(2-aminoethyl)-N,N',N'-trimethylethanediamine while keeping the temperature of the reaction mixture below 30° C. The mixture is stirred under a nitrogen atmosphere for 18 h. To this mixture is added 20.0 g of potassium carbonate followed by 18.2 g of dimethyl sulfate over 0.5 h. The mixture is then stirred 48 h at room temperature, filtered, and precipitated with ether. The precipitate is dissolved in 500 mL $H_2O$ and acidified with 66 mL of concentrated hydrochloric acid. The solution is dialyzed as per Ex. I until the effluent is pH=3. An additional 66 mL of concentrated hydrochloric acid is added and the solution is redialyzed until the effluent is pH=6. The solution is concentrated by dialysis to 100 mL and lyophilized to afford the water soluble title compound.

% Cl Calc., 20.65 Found 15.37
Cl/N Calc., 1.27 Found 1.04
C/N Calc., 2.79 Found 3.05

EXAMPLE XI

In a manner similar to Example X, the following reactants:
a) N-(2-aminoethyl)-N-,N',N'-trimethyl-1,3-propanediamine and
b) 4-methyl-1-piperazinethanamine, are reacted with polyanhydroaspartic acid and quaternized with dimethyl sulfate to produce respectively:

c) poly[imino[1-[[[[2-[[3-(trimethylammonio)propyl] dimethylammonio]ethyl]amino]carbonyl]methyl]-2-oxo-1,2-ethanediyl dichloride]] and d) poly[imino[1-[[[[2-( 1,4,4-trimethylpiperazinium-1-yl)ethyl]amino]carbonyl]methyl]-2-oxo- 1,2-ethanediyl dichloride]].

EXAMPLE XII

Poly[imino[1-[[[[3-(trimethylammonio) propyl]amino]carbonyl] methyl]-2-oxo-1,2-ethanediyl chloride]],

[RS], Crosslinked with 15% 1,3-propanediamine 5.0 g of polyanhydroaspartic acid is dissolved in 50 mL of DMSO. 0.57 g of 1,3-propanediamine (A) is added and the mixture is heated for 2 h at 75° C. under a nitrogen atmosphere. The reaction mixture is cooled to room temperature and 28.6 g of N,N-dimethyl-1,3-propanediamine (B) is added. The mixture is stirred for 1 h at room temperature, 18 h at 75° C., then cooled to room temperature and precipitated with ether. The precipitate is dissolved in 50 mL of DMF, and to this solution is added 35.6 g of potassium carbonate and 32.5 g of dimethyl sulfate. The mixture is stirred for 1 h at 75° C., then 18 h at room temperature and then filtered and precipitated with ether. The precipitate is dissolved in 500 mL $H_2O$ and acidified with 45 mL concentrated hydrochloric acid. The solution is dialyzed as per Ex. I until the effluent is pH=3. An additional 45 mL of concentrated hydrochloric acid is added and the solution is redialyzed until the effluent is pH=6. The solution is concentrated by dialysis to 100 mL and lyophilized to afford the water soluble title compound.

% Cl Calc., 13.59 Found 10.68
Cl/N Calc., 0.77 Found 0.64
C/N Calc., 2.72 Found 2.82

EXAMPLE XIII

Polymers that may potentially have varying degrees of branching or cross-linking can be prepared by adjusting the ratio of the diamines. Thus polymers wherein the reacting diamine (A):(B) ratios are:

a) 1:99,
b) 2.5:97.5,
c) 5:95,
d) 7.5:92.5 and
e) 10:90, can be prepared in a manner similar to Example XII by reacting the respective amounts of 1,3-propanediamine and N,N-dimethylpropanediamine with polyanhydroaspartic acid to obtain respectively:

f) poly[imino[1-[[[[3-(trimethylammonio )propyl] amino] carbonyl]methyl]-2-oxo-1,2-ethanediyl chloride]], [RS], crosslinked with 1% 1,3-propanediamine, g) poly[imino[1-[[[[3-(trimethylammonio )propyl]amino] carbonyl]methyl]-2-oxo-1,2-ethanediyl chloride]], [RS], crosslinked with 2.5% 1,3-propanediamine, h) poly[imino[1-[[[[3-(trimethylammonio )propyl]amino] carbonyl]methyl]-2-oxo-1,2-ethanediyl chloride]], [RS], crosslinked with 5% 1,3-propanediamine, i) poly[imino[1-[[[[3-(trimethylammonio )propyl]amino] carbonyl]methyl]-2-oxo-1,2-ethanediyl chloride]], [RS], crosslinked with 7.5% 1,3-propanediamine, and j) poly[imino[1-[[[[3-(trimethylammonio )propyl]amino] carbonyl]methyl]-2-oxo-1,2-ethanediyl chloride]], [RS], crosslinked with 10% 1,3-propanediamine.

EXAMPLE XIV

Poly[imino[1-[[[[3-hydroxylpropyl]amino]carbonyl] methyl]- 2-oxo-1,2-ethanediyl]imino[1-[[[[3 -(trimethylammonio)propyl] amino]carbonyl]methyl]-2-oxo-1,2-ethanediyl chloride]]

4.0 g of polyanhydroaspartic acid is dissolved in 50 mL of anhydrous DMF and added to 1.55 g of 3-aminopropanol (A). The mixture is stirred at room temperature for 3 h, and 4.21 g of N,N-dimethyl-1,3-propanediamine (B) is added and the reaction mixture is stirred for 18 h. To this solution is added 45.6 g of potassium carbonate and 41.6 g of dimethyl sulfate over 0.5 h. The mixture is stirred 18 h at room temperature, filtered, and precipitated with ether. The precipitate is dissolved in 500 mL $H_2O$ and acidified with 30 mL of concentrated hydrochloric acid. The solution is dialyzed as per Ex. I until the effluent is pH=3. An additional 30 mL of concentrated hydrochloric acid is added and the solution is redialyzed until the effluent is pH=6. The solution is concentrated by dialysis to 100 mL and lyophilized to afford a water soluble solid.

% Cl Calc., 8.42 Found 6.46
Cl/N Calc., 0.51 Found 0.41
C/N Calc., 2.82 Found 2.92

EXAMPLE XV

Poly[imino[1-[[[[3-hydroxylpropyl]amino]carbonyl] methyl]-
2-oxo-1,2-ethanediyl]imino[1-[[[[3-(trimethylammonio) propyl]amino]
carbonyl]methyl]-2-oxo-1,2-ethanediyl chloride]]

In a manner similar to Example XIV, a copolymer of Formula 7 with R=OH, wherein (A):(B)=1:2 can be prepared by reacting first 1.03 g of 3-aminopropanol then 6.5 g of N,N-dimethyl-1,3-propanediamine with 4.0 g poly-anhydroaspartic acid, followed by quaternization.

EXAMPLE XVI

Poly[imino[1-[[[[3-(pyridinium-1-yl)propyl]amino] carbonyl]methyl- 2-oxo-1,2-ethanediyl chloride]]

To a solution of 11.0 g of 3-aminopropylpyridinium chloride hydrochloride in 10 mL $H_2O$ and 40 mL of DMF are added in succession 8.0 mL of triethylamine and 2.0 g of polyanhydroaspartic acid. The reaction mixture is stirred for 72 h at room temperature then precipitated with ether. The precipitate is dissolved in 500 mL of $H_2O$, dialyzed and lyophilized to afford the water soluble title compound.

Cl Calc., 13.14 Found 8.81
Cl/N Calc., 0.97 Found 0.61
C/N Calc., 3.94 Found 3.44

EXAMPLE XVII

Poly[imino[1-[2-[[[3-(trimethylammonio)propyl] amino]carbonyl] ethyl]-2-oxo-1,2-ethanediyl chloride]]

2.0 g of poly (γ-methyl L-glutamate) is suspended in 30 mL of N,N-dimethyl- 1,3-propanediamine and stirred under a nitrogen atmosphere for 5 days at 80° C., then precipitated with ether. The precipitate is dissolved in 100 mL of DMF, and to this solution is added 8.8 g of dimethyl sulfate, then after 20 minutes 9.7 g of potassium carbonate. The mixture is stirred 18 h at room temperature and the mixture is poured into ether. The solids are dissolved in 800 mL of $H_2O$ and dialyzed until the effluent is pH=8.5. The aqueous solution is acidified with 25 mL of 6N hydrochloric acid, dialyzed Until the effluent is pH=3, reacidified with 25 mL of 6N hydrochloric acid and dialyzed until the effluent is pH=6. The solution is concentrated to 100 mL and lyophilized to afford the water soluble title compound.

% Cl Calc., 13.44 Found 10.71
Cl/N Calc., 0.84 Found 0.66
C/N Calc., 3.14 Found 3.01

EXAMPLE XVIII

Poly[imino[1-[[[[3-(trimethylammonio)propyl] amino]carbonyl] methyl]-2-oxo-1,2,ethanediyl chloride]][ R], crosslinked with 0.2–0.5
(—$CH_2CH$=$CHCH_2$—)

3.5 g of polyanhydroaspartic acid is dissolved in 30 mL of anhydrous DMF and added dropwise to 9.2 g of N,N-dimethyl-1,3-propanediamine while keeping the temperature of the reaction mixture below 30° C. The mixture is stirred under a nitrogen atmosphere for 18 h at room temperature, then precipitated with a mixture of ether and petroleum ether. The precipitate is dissolved in a minimum amount of methanol and reprecipitated with ether. The precipitate is dissolved in 500 mL $H_2O$, dialyzed, and lyophilized to afford 4.7 g of an amber solid. This solid is dissolved in 50 mL DMF, and to this solution is added 0.44 g of cis-1,4-dichloro-2-butene. The mixture is stirred for 4 h at 50° C., then 5.0 mL of dimethyl sulfate and 7.0 g of potassium carbonate are added and the mixture is stirred 18 h at 50° C. The reaction mixture is then cooled to room temperature, filtered and precipitated with ether. The precipitate is dissolved in 500 mL $H_2O$ and acidified with 25 mL of concentrated hydrochloric acid. The solution is dialyzed as per Ex. I until the effluent is pH=3. An additional 25 mL of concentrated hydrochloric acid is added and the solution is redialyzed until the effluent is pH=6. The solution is concentrated by dialysis to 100 mL and lyophilized to afford the water soluble title compound.

% Cl Calc., 14.06 Found 11.27
Cl/N Calc., 2.91 Found 2.98
C/N Calc., 0.84 Found 0.77

EXAMPLE XIX

Control of Molecular Weight of
Poly[imino[1-[[[[2-[[2-(trimethylammonio)ethyl] dimethylammonio]ethyl]amino]carbonyl]methyl]-2-oxo-1,2-ethanediyl dichloride]]

This example illustrates some of the means by which the degree of polymerization, and hence the molecular weight distribution, may be controlled. Polyanhydroaspartic acid of reduced viscosity =15.2 mL/g (determined on a 0.5% solution in N,N-dimethylformamide) (4.0 g; 41.2 mmol of monomer unit) is dissolved in N,N-dimethylformamide (20 mL). The solution is treated with $N^2$-(2-aminoethyl)-$N^1$,$N^1$-dimethyl-1,2-ethanediamine (6.1 g, 43.3 mmol) at the temperature temp(1) for time(1), as specified in Table V below. The reaction mixture is then maintained at the temperature temp(2) for time(2). Potassium carbonate (21.62 g, 157 mmol) is added, followed by dimethyl sulfate (19.74 g, 157 mmol), and the mixture is stirred at 47° C. for 16 h. The mixture is cooled to room temperature, concentrated ammonium hydroxide (2.8 mL) is added, and the mixture is stirred for 1 h. Water (50 mL) is added, and the mixture stirred for 30 min and then allowed to settle for 1 h. The lower layer is separated and discarded. The upper layer is added to acetone (360 mL) with stirring. The supernatant is decanted, and the residue dissolved in water (410 mL). Concentrated hydrochloric acid (34.3 mL, 412 mmol) is added, and the solution is kept at room temperature for time(3). The solution is then ultrafiltered, using membranes with a nominal molecular weight cutoff of NMWL, until the solution showed pH=5.5; the solution volume is kept constant by addition of deionized water. A second, equal portion of concentrated hydrochloric acid is added, and the solution immediately ultrafiltered as before. The resulting solution is concentrated on the dialyzer to a volume of 100 mL, and freeze dried to afford the product.

The molecular weight distribution of the product is studied by size exclusion chromatography, using the following columns connected in series:

Guard column: 50×4.6 mm, packed with CATSEC 300 A.

Column 1:250×4.6 mm, packed with CATSEC 300 A.

Columns 2 and 3:250×4.6 mm, packed with CATSEC 100 A.

Elution is performed with 0.2M sodium chloride in 0.1% aqueous trifluoroacetic acid at a flow rate of 0.3 mL/min, using UV detection at 200 nm. $M_{sec}$, the molecular weight at the peak maximum, is estimated using calibration curves from poly(vinylpyridine) standards. $M_{sec}$ and the derived degree of polymerization n are presented in Table V below.

TABLE V

| temp (1) | time (1) | temp (2) | time (2) | time (3) | NMWL | $M_{sec}$ | n |
|---|---|---|---|---|---|---|---|
| 58° C. | 6 h | 24° C. | 10 h | 12 days | 30,000 | 8,200 | 30 |
| 58° C. | 6 h | 24° C. | 10 h | 12 days | 10,000 | 5,400 | 20 |
| 25° C. | 3 days | — | — | 4 h | 10,000 | 17,000 | 62 |
| 40° C. | 3 days | — | — | 4 h | 10,000 | 11,000 | 40 |
| 25° C. | 8 h | — | — | 4 h | 10,000 | 23,000 | 84 |

We claim:

1. The method of inhibiting the growth of gram positive bacteria in a subject in need thereof which comprises administering to said subject a gram positive inhibitory amount of a compound of the following structural Formula II:

$$\begin{array}{c} R \\ | \\ HN-(CH_2)_y-(CH)_t-(CH_2)_z-Q \\ | \\ CO \\ | \\ (CH_2)_w \quad X^- \\ | \\ +NH-C_2H_3-CO\}_n \end{array}$$

wherein w is the integer 0 or 1;

y is the integer 1–6;

z is the integer 0–3;

t is the integer 0 or 1;

Q is 
$-{}^+N\begin{array}{c}R_1\\-R_2\\R_3\end{array}$,  
$-N^+\underset{R_4}{\underbrace{\phantom{xxx}}}N-R_3$,  
$R_3-N^+\underset{\phantom{x}}{\underbrace{\phantom{xxx}}}N-R_3$, $-N\underset{\phantom{x}}{\underbrace{\phantom{xxx}}}R_4$,  
$\underset{\phantom{x}}{\underbrace{\phantom{xxx}}}N-R_3$,  
$-NH-\overset{N-R_5}{\overset{\|}{C}}-NHR_6$ or -continued $$\begin{array}{c} R_1 \\ / \\ B-{}^+N-R_2 \\ \backslash \\ R_3 \end{array}$$ (phenyl)

R is hydrogen, lower alkyl, phenyl or when taken together with $R_1$ forms a saturated monoheterocyclic ring of from 5 to 6 members;

$R_1$, $R_2$ are the same or independently $C_1$-$C_{10}$ straight or branched chain alkyl which may be substituted by up to 3 substituents selected from 1 to 2 hydroxyl groups and one $$-{}^+N\begin{array}{c}R_3\\-R_7\\R_8\end{array}$$

group, or when taken together form a saturated heterocyclic ring of from 5 to 6 members which may contain a $$\begin{array}{c} + \\ -N-R_7 \\ / \quad \backslash \\ R_3 \quad R_3 \end{array}$$

or —O— linkage;

$R_3$ is methyl, ethyl, benzyl which may be substituted by up to 3 substituents selected from hydroxyl, halogen, methoxy and $C_1$-$C_6$ straight or branched chain alkyl, 1-naphthyl or 2-naphthyl;

$R_4$ is a $C_1$-$C_6$ straight or branched chain alkyl which may be substituted by one hydroxyl group;

$R_5$, $R_6$ are the same or independently hydrogen, $C_1$-$C_4$ straight or branched chain alkyl or when taken together form a diheterocyclic ring of from 5 to 6 members;

$R_7$, $R_8$ are the same or independently $C_1$-$C_6$ straight or branched chain alkyl which may be substituted by one hydroxyl group or when taken together with an —O— linkage form a morpholine ring;

B is a direct link or a $C_1$-$C_4$ straight or branched chain alkyl;

n is an integer in the range from about 5 to 500; and $X^-$ is an anion forming a pharmaceutically acceptable salt.

2. The method of claim 1 where n is in the range of from about 5 to 49.

3. The method of claim 1 where n is in the range of 50 to 500.

4. The method of claim 2 wherein the compound administered is poly[ imino[1-[[[[3-(trimethylammonio)propyl]amino]carbonyl]methyl]-2-oxo-1,2-ethanediyl chloride]].

5. The method of claim 2 wherein the compound administered is poly *imino*[1-[[[[2-[[2-(trimethylammonio)ethyl]dimethylammonio]ethyl]amino] carbonyl]methyl]-2-oxo-1,2-ethanediyl chloride]].

6. The method of claim 2 wherein the compound administered is poly[ imino[1-[[[[3-[dimethyl(phenylmethyl)ammonio]propyl]aminocarbonyl]methyl]- 2-oxo-1,2-ethanediyl chloride]].

7. The method of claim 2 wherein the compound administered is poly *imino*[1-[[[[3-[(aminoiminomethyl)amino]propyl]amino]carbonyl]methyl]-2-oxo- 1,2-ethanediyl hydrochloride]].

8. The method of claim 2 wherein the compound administered is [S]-poly[ imino[1-[[[[3-(trimethylammonio)propyl]amino]-carbonyl]methyl]-2-oxo- 1,2-ethanediyl chloride]].

9. The method of claim 3 wherein the compound administered is poly[imino[ 1-[[[[3-(trimethylammonio)propyl]amino]carbonyl]methyl]-2-oxo-1,2-ethanediyl chloride]].

10. The method of claim 3 wherein the compound administered is poly[imino[ 1-[[[[2-[[2-(trimethylammonio)ethyl]dimethylammonio]ethyl]amino] carbonyl]methyl]-2-oxo-1,2-ethanediyl chloride]].

11. The method of claim 3 wherein the compound administered is poly[imino[ 1-[[[[3-[dimethyl(phenylmethyl)ammonio]propyl]aminocarbonyl]-methyl]- 2-oxo-1,2-ethanediyl chloride]].

12. The method of claim 3 wherein the compound administered is poly[imino[ 1-[[[[3-[(aminoiminomethyl)amino]propyl]amino]carbonyl]methyl]-2-oxo- 1,2-ethanediyl hydrochloride]].

13. The method of claim 3 wherein the compound administered is [S]-poly[ imino[1-[[[[3-(trimethylammonio)propyl]amino]-carbonyl]methyl]-2-oxo- 1,2-ethanediyl chloride]].

14. The method of inhibiting the growth of gram-positive bacteria on a surface which comprises contacting the surface with a gram positive inhibitory amount of a compound of the following structural Formula II:

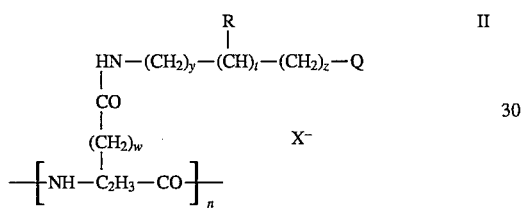

II wherein w is the integer 0 or 1;

y is the integer 1–6;

z is the integer 0–3;

t is the integer 0 or 1;

contain a

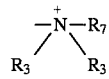

or —O— linkage;

$R_3$ is methyl, ethyl, benzyl which may be substituted by up to 3 substituents selected from hydroxyl, halogen, methoxy and $C_1$–$C_6$ straight or branched chain alkyl, 1-naphthyl or 2-naphthyl;

$R_4$ is a $C_1$–$C_6$ straight or branched chain alkyl which may be substituted by one hydroxyl group;

$R_5$, $R_6$ are the same or independently hydrogen, $C_1$–$C_4$ straight or branched chain alkyl or when taken together form a diheterocyclic ring of from 5 to 6 members;

$R_7$, $R_8$ are the same or independently $C_1$–$C_6$ straight or branched chain alkyl which may be substituted by one hydroxyl group or when taken together with an —O— linkage form a morpholine ring;

B is a direct link or a $C_1$–$C_4$ straight or branched chain alkyl;

n is an integer in the range from about 5 to 500; and $X^-$ is an anion forming a pharmaceutically acceptable salt.

* * * * *